United States Patent
Papageorge (10) Patent No.: US 6,584,445 B2
(45) Date of Patent: Jun. 24, 2003

(54) MEDICAL SYSTEM FOR SHARED PATIENT AND PHYSICIAN DECISION MAKING

(75) Inventor: Basil Papageorge, Los Angeles, CA (US)

(73) Assignee: Computerized Health Evaluation Systems, Inc., Los Angeles, CA (US)

(*) Notice: Subject to any disclaimer, the term of this patent is extended or adjusted under 35 U.S.C. 154(b) by 0 days.

(21) Appl. No.: 09/846,176

(22) Filed: Apr. 30, 2001

(65) Prior Publication Data

US 2002/0184050 A1 Dec. 5, 2002

Related U.S. Application Data

(63) Continuation of application No. 09/178,073, filed on Oct. 22, 1998, now abandoned.

(51) Int. Cl.[7] ............................ G06F 17/60; G06F 17/00
(52) U.S. Cl. ............................ 705/3; 705/2; 434/226
(58) Field of Search ........................ 705/2, 3; 434/236

(56) References Cited

U.S. PATENT DOCUMENTS

| | | | | |
|---|---|---|---|---|
| 5,301,105 A | * | 4/1994 | Cummings, Jr. ............... | 705/2 |
| 5,517,405 A | * | 5/1996 | McAndrew et al. ........... | 706/45 |
| 5,519,607 A | * | 5/1996 | Tawill ............................ | 705/2 |
| 5,572,421 A | * | 11/1996 | Altman et al. ................. | 705/3 |
| 5,594,638 A | * | 1/1997 | Iliff ................................ | 705/3 |
| 5,724,379 A | * | 3/1998 | Perkins et al. ................. | 705/2 |
| 5,915,240 A | * | 6/1999 | Karpf ............................. | 705/2 |
| 5,918,208 A | * | 6/1999 | Javitt ............................. | 705/2 |
| 5,953,704 A | * | 9/1999 | McIlroy et al. ................ | 705/2 |
| 6,014,631 A | * | 1/2000 | Teagarden et al. ............. | 705/3 |
| 6,029,138 A | * | 2/2000 | Khorasani et al. ............. | 705/2 |
| 6,047,259 A | * | 4/2000 | Campbell et al. .............. | 705/3 |
| 6,061,657 A | * | 5/2000 | Whiting-O'Keefe ........... | 705/2 |
| 6,063,028 A | * | 5/2000 | Luciano ......................... | 600/300 |
| 6,081,786 A | * | 6/2000 | Barry et al. .................... | 705/3 |
| 6,108,635 A | * | 8/2000 | Herren et al. .................. | 705/2 |
| 6,269,339 B1 | * | 7/2001 | Silver ............................. | 705/2 |
| 6,443,734 B1 | * | 9/2002 | Rappaport ..................... | 434/236 |

FOREIGN PATENT DOCUMENTS

WO WO97/15022 * 4/1997 ........... G06F/19/00

OTHER PUBLICATIONS

Rosenfeld, Barry D., White, Mary, and Passik, Steven D.; "Making Treatment Decisions with HIV Infection: A Pilot Study of Patient Preferences", Jul. 1997, Medical Decision Making, v 17, n 3, pp 307–314.*

Owens, DK; "Patient Preferences and the Development of Practice Guidelines", May 1998, Spine, v 23, n 9, 1 pg (Abstract only).*

McCombs, Jeffrey Scott; "Physician Price and Treatment Decisions: A Multiple Treatments Model", Jan. 1982, Dissertation Abstracts International, v 43/03–A, 1 pg (Abstract only).*

Frosch, Dominick et al., Shared Decision Making in Clinical Medicine: Past Research and Future Directions, American Journal of Preventive Medicine, 1999, pp. 285–294, vol. 17, No. 4.

* cited by examiner

Primary Examiner—James W. Myhre
(74) Attorney, Agent, or Firm—Christie, Parker & Hale, LLP (57) ABSTRACT

A computerized health evaluation system for joint patient and physician decision making concerning particular medical diseases and conditions. The system includes a computer system with a patient input module for patient input of patient data concerning the patient's lifestyle and preferences, a physician input module for physician input of physical and physiological data, and a database of the latest medical findings concerning the particular disease and condition. The computer system uses an algorithm for weighing the patient data and the physician data in view of the database and generating a report setting forth various treatment options. Based upon the report, the patient and physician will jointly decide on a treatment approach.

8 Claims, 3 Drawing Sheets

CHES METHOD

FIGURE 1

PATIENT DIAGNOSED WITH CHRONIC MITRAL VALVE DISEASE
Treatment selection process with and without Invention

MEDICAL SYSTEM FOR SHARED PATIENT AND PHYSICIAN DECISION MAKING

CROSS-REFERENCE TO RELATED APPLICATION

This patent application is a continuation of patent application Ser. No. 09/178,073, filed Oct. 22, 1998 now ABN entitled MEDICAL SYSTEM FOR SHARED PATIENT AND PHYSICIAN DECISION MAKING.

BACKGROUND OF THE INVENTION

1. Field of the Invention

This invention relates to the field of medical systems for helping patients make informed medical decisions, and more particularly to a computerized health evaluation system (CHES) that involves full patient participation in selecting among various treatment options for particular medical conditions and a shared decision-making process with a physician in order to allow the best possible medical treatment to be carried out, considering the patient's lifestyle and other patient preferences along with that patient medical condition as entered by the physician and the most up-to-date medical data concerning that medical condition.

2. Description of the Prior Art

Many medical conditions have two or more treatment paths, each with generally different costs and different outcomes and risks depending on the patient's particular circumstances. Included among these conditions is mitral valve disease. It is known that knowledge of direct and indirect treatment costs permits patients to assess the economic impact of their treatment choices and affects their treatment preferences. Moreover, it is known that cost-sharing lowers the overall utilization of the medical system. Accordingly, it may be that knowledge of treatment costs without an understanding of treatment effectiveness can negatively impact health.

There has been a considerable amount of research dedicated to the issue of the role of the patient in selecting a treatment choice. Studies indicate that patients tend to value their doctor's recommendations more in cases with more severe or life-threatening conditions. However, patients generally wish to take part in medical decisions concerning their health.

In an era of rising medical costs and greater demands on physicians to deliver better care at a lower cost, many physicians, particularly those who do not specialize in particular diseases and conditions, are not always abreast of the most current medical findings and data. Even when physicians are fully aware of the various treatment options, they presently do not have the tools which allow them to work with their patients to help jointly select the best treatment based upon the latest statistical findings, cost factors, and their patient's expressed lifestyle choices and preferences. Indeed, knowledge about diseases and their treatments is expanding faster than can be absorbed. Compounding this fact is the diversity in interpreting medical knowledge due to physician differences in training, experience, and peer influence. To be most effective, a physician should be aware of all available information. This calls for clinician access to up-to-date information services such as computer data banks.

Each possible treatment for a given condition has a unique clinical and non-clinical impact. One way to evaluate outcomes for treatment effectively before selecting one is to use economic rules which explain human needs and behavior. As used here, the term "economic" includes monetary costs, the values of other factors, and opportunity costs which differ with each patient. These rules can be used to rate one's desires and priorities, to identify a preferred solution. Since one solution may not be ideal as other possible solutions, a way to access all possible solutions is needed to reveal the one which will achieve the optimal outcome.

Computers can be programmed with specific data management rules. These rules need validation by collecting treatment outcome data from the medical literature; statistically analyzing them to verify diverse practice patterns for the same condition; and having medical experts in each area interpret these results. These experts can provide a consensus on the dynamics of a disease and the implications of its different forms of treatment. They can also help identify which clinical parameters would indicate when major intervention is actually needed.

With these rules, computers can be used to assess each patient's status and how it may be uniquely impacted by each treatment. This evaluation must include a broad range of data that cannot be manually collected and assimilated for each patient. Thus, consistency is achieved by using computers to repeat complex tasks with equal accuracy. This permits reliability in the analysis and in formatting of the results without human error.

Computers cannot fully answer questions dealing with clinical, economic, family concerns, and other varied issues. They can, however, manage data on these issues, expressly: what numeric measure to give to certain data, what data sets to use, what values to compute, and with what formulas. Computers can also be encoded to format its assessment in a printout of information that can be easily interpreted. The computerized health evaluation system CHES of the invention uses these capabilities in its systems.

Under the approach of the invention, the patient can input individual information and concerns/desires, and the physician will input clinical data and a preliminary treatment plan, if any, for the patient. Thus, the patient will more actively be participating in the decision making process, yet still maintain his or her doctor's position on treatment.

Three major parties are affected by the selection of a given treatment. Each has inadequate information with which to optimize their "return" from the treatment of a given medical condition. The following is a summary of the issues they face:

A. The Problem:

1. Patients

This consumer has limited clinical knowledge. The patient often does not know what questions to ask when a diagnosis is made and a treatment is recommended. S/He will not know all of the treatment options. Trying to consider non-clinical risks linked to both the condition and each possible treatment adds to the confusion. For example, what are the true trade-offs in delaying treatment? What are the potential negative consequences of a given treatment to a patient's family and career, and their probability of occurring? Patients often have no means to assess these issues in the context of their unique circumstances.

2. Physicians

The physician diagnoses and prescribes treatments, but often has little time to inform the patient about the possible effects of the condition, all possible treatments, and their potential positive and negative outcomes. The physician also may not know every non-clinical factor of each patient that may affect the choice of treatment. He must make critical decisions under much uncertainty. These uncertainties, (e.g.

surgical risks, treatment outcomes, non-clinical impact), and the concerns of the patient, (e.g. impact on family, income loss) complicate the decision-making process. Thus, an unsuitable treatment may be selected without a mechanism for identifying, measuring, or fully assessing all relevant factors.

3. Third Party Payer (Insures/Employers)

These entities are outside the clinical decision-making process to avoid a conflict of interest. However, they are directly affected by treatment decisions due to their high costs, especially from poor outcomes. Recent California legislation allows insurers to confirm the need for hospitalization (Pre-Admission certification). Yet, there is no systematic way to verify what treatments are the most appropriate both clinically and economically.

B. Attempted Solutions:

To address these issues, various studies are now under way to identify the most effective treatments for given conditions based on outcomes. This outcomes research will set new practice patterns regarding treatments. This has some value in emphasizing outcomes over the process or structure of health care as a measure of quality. There is a risk, however, of strictly using treatments deemed most clinically effective, instead of offering treatments based on what each patient needs, clinically and non-clinically. Since patients are not identical, the most effective treatment is that which offers clinical improvement, and preserves quality of life, which differs in each case.

Efforts to identify unnecessary treatments is now popular in trying to reduce health care costs by withholding coverage for such treatments, unless physicians can justify their use. While these limits can generate short-term cost savings, such efforts intrude on the physician-patient relationship, and can be harmful if the condition requires the treatment, but does not meet a set criteria. Since each patient is unique, with different needs beyond his/her clinical status, rationing treatments based on strict criteria often raises health care costs and lowers patient satisfaction.

In-patient ancillary services have also been restricted, again based on predetermined criteria. If there is little flexibility for complications during stays, or if extending the stay is not properly justified, the patient is again jeopardized. The question is whether to control costs by limiting the use of resources, or whether to improve the chances that the patient is receiving the correct and timely treatment. The latter would reduce costs by avoiding morbidity or mortality resulting from improper treatment and/or restricted use of health care resources.

Limiting services emphasizes the process of health care rather than outcomes (e.g. extended survival, reduced morbidity, or increased productivity of the patient), which are not considered when services are sought or paid for. This is because the issues involved appear too diverse and complex in relation to one another to allow their careful consideration as part of the decision-making process. Since current technology has not been filly exploited in complex problem analysis, rudimentary, restrictive criteria are used to control costs, without assessing a treatment's value in terms of its short- and long-term effects relative to its alternatives.

There accordingly remains a need for a tool designed to help patients reach the best treatment options taking into consideration the patient's lifestyle and personal choices, the cost and effectiveness, and the physician's by assessing each option in terms of patient specific data.

SUMMARY OF THE INVENTION

One object of the present invention is to provide a tool designed to help patients reach the best treatment options taking into consideration the patient's lifestyle and personal choices, the cost and effectiveness, and the physician's assessment of each option in terms of patient specific data.

Another object of the invention is to provide a medical decision system wherein the patient can input individual information and concerns/desires, and the physician will input clinical data and a preliminary treatment plan, if any, for the patient, to develop various treatment options with the costs and benefits.

Yet another aspects of the invention is to provide a computerized health evaluation system which allows for full patient participation in treatment selection and a shared decision-making process with physicians in order to choose among different costs and post-treatment outcomes.

The computerized health evaluation system permits the patient's unique circumstances, as determined by the physician and patient to be are entered into the system. This information is processed by the system which has statistical information about the particular medical condition, the various treatment options, the treatment effectiveness, financial impact, and current disease-related data from the medical literature. The system outputs a report which presents the various kinds of information for evaluation by the patient and doctor for a discussion and review session. The system then allows complex medical decisions to be made more effectively and with more confidence.

These and other objects of the invention are provided by the system which i) includes a large patient role in treatment choice based upon the patient's lifestyle and other choices, ii) patient/physician shared decision making, iii) patient/physician communication, iv) patient education and informing, and v) computer technology to facilitate decision discussion and the decision-making process.

These and other objections of the invention are described with reference to mitral valve disease, as an example. Mitral valve disease presently has two surgical treatment approaches with different financial costs and outcomes associated with each of the two procedures. The method of the invention is applicable to any number of medical conditions having multiple treatment regimens, including, for example, prostate cancer, breast cancer.

DESCRIPTION OF THE PREFERRED EMBODIMENT

The computerized health evaluation system and method CHES of the invention, provides a comprehensive way to help avoid the problems in clinical decision-making and the limitations of the cost-containment efforts described above. By using CHES, the patient learns about his/her condition, and the potential risks and benefits of each possible treatment. CHES measures these risks and benefits so that the patient can more easily assess them, especially the non-clinical factors that may be affected. Thus, the patient can more informatively participate in the decision-making process. The physicians are informed of what the patient knows. The system also provides the latest medical data on the condition at issue and the outcome of each treatment. They are thus better able to work with the patient in selecting the most appropriate treatment. The Insurer also benefits because CHES enables the review of all possible treatments and their costs. Using a different treatment in each case will reduce costly negative outcomes, permitting cost savings.

A critical issue in providing treatment advice is informed consent. Patients can share in the decision-making process only if they have enough information about their condition and the potential results of each treatment. There have been court decisions finding a physician who had treated a patient without adequate disclosure of the risks of treatment liable for negligence. In California, informed consent is measured by what the patient needs to know to make an informed decision.

Patients using CHES are given both general information about their condition and specific data about the clinical and non-clinical effects of each treatment option. Thus, they can take more responsibility for the treatment selected. All parties affected by the decision thus benefit by the pertinent information that CHES can add to the decision-making process, which minimizes the uncertainty of deciding whether, when, and what type of treatment to pursue.

The CHES systems can show physicians and patients the probable outcomes of each treatment strategy. While most strategies are valid, clinicians verify that crucial, non-clinical factors are not included in treatment decisions due to the difficulty in evaluating family, social, and economic factors together with clinical considerations.

The systems will aid patients needing treatment by evaluating his/her type of a given disease, its severity, symptoms, and examination and test results (e.g., in the case of mitral valve disease [MVD] hemodynamic data, EKG, echocardiogram, left ventricular function, and other clinical indicators). This data will be entered by the physician, along with his/her opinion of the patient's condition and any reason(s) for preferring one treatment over another. The patient will indicate the type and the degree of symptoms s/he is experiencing and his/her present functional status, how it affects his/her work, family, life-style, and immediate and long-term plans.

CHES assesses these data in real time and generates a report on the results, which is sent to physicians and/or patients as requested. The report summarizes the data from the users, with conditional text on how each response affects the course of the disease and the probable results of each treatment option. It will help physicians and patients assess the utility of each treatment and their trade-offs. It also gives estimated direct costs of each option (which vary based on different morbidity and mortality rates by the specific form of a disease) and indirect costs, (i.e., the patient's income earning/loss potential before and after treatment). Insurers are sent a summary of this report showing the treatment preferred, its potential costs compared to others, the reasons for its selection, how it compares to what the medical literature shows to be effective, and why, in some cases, a less optimal approach from a clinical and/or cost perspective may be required.

CHES identifies each patient's unique factors, which often conflict with the utility of the "clinically most effective" treatment. Since such treatments may not serve a patient's needs, alternatives, with their positive and negative implications, should be considered, especially if any of them better meets the patient's needs. CHES provides this assistance.

The uniqueness of CHES may raise some concern. Some clinicians may think it intrudes on their judgement. Others may feel that it will dictate treatments contrary to their practice style. Yet, insurers and UR firms now influence health services (e.g., cutting hospital days and ancillary services, raising coinsurance rates, and disapproving procedures which are, by their set criteria, unnecessary) in trying to control costs. None of these mechanisms have proven to be completely effective in stemming health care costs. In contrast, CHES helps physicians document their treatment plans, with added information on their patients and the latest outcome data available.

CHES concurs with the federal initiative on outcomes research find the most effective treatment for each condition in order to set practice patterns where the "most effective treatment" is used. CHES exceeds the emphasis on outcomes by recognizing that the most effective treatment will differ in each case. The right treatment for each patient must be identified, based on the stage of disease and the clinical and non-clinical implications of each option. CHES integrates these factors regardless of what is "usually" efficacious.

CHES uniquely assesses costs and outcomes of all treatments, and their impact on the patient's situation. If "customary" treatments, which are not always suitable, are used, the true cost of health care will continue to escalate. This is due to morbidity and mortality levels, and their costs, which could have been avoided by using other treatments. Poor treatment outcomes raise these costs when alternatives may have had better results (i.e., fewer complications, lower mortality, and, thus, restored patient productivity). These possible events can be minimized if physicians and patients use data on specific treatments to make more informed choices. CHES provides this data which can control costs and preserve quality of care.

The UR firm, Intracorp, of Philadelphia, Pa., works to save insurers money by reducing hospital stays. Value Health Sciences, Inc., of Santa Monica, Calif., provides software that identifies certain "unneeded" surgeries. Other UR firms make physicians justify much of the care they prescribe. Second opinion programs are no longer deemed effective in lowering costs. All these efforts may raise health care costs, add more bureaucracy to the system, and potentially place the patient at higher risk because certain services are arbitrarily disapproved. In contrast, CHES helps physicians and patients make informed treatment choices without more bureaucratic expense or outside influence. It also reduces third party oversight since the need for a treatment is documented through using CHES.

The effect of the innovative approach of CHES on "the bottom line" of health care cost will be significant. In the case of mitral valve disease, for example, mitral valve replacement (MVR) with higher morbidity and mortality rates still outpaces repairs which could be more effective for many patients at considerable savings (at least 50 percent).

How CHES Works

CHES will be available through an on-line service that can be accessed by physician and patient users through various means (e.g. the Internet). These may include, but are not limited to, computer access by modem, touch-tone telephone keypad (potentially) with written and voice instructions, and/or via interactive multimedia for which other consumer applications are being designed. For those users who do not prefer or do not have access to such technologies, questionnaire forms can be used, with answer sheets returned to CHES for processing using scanning equipment.

On electronic platforms, the patient will read screen text explaining the disease and all treatment options. After reading this overview, the patient then answers the questionnaire, using single keystrokes to select choices. This feature will maximize the number of patients who will use the system. The patient is asked about his/her functional status and how much it may be impaired; whether work, family, lifestyle, and/or future plans are affected; and treatment preferences, given the different probable risks associated with each one.

The patient's answers are automatically saved in a file under his/her own identification code. The patient's responses are stored in a patient input module. The physician uses this confidential code to access the file and similarly complete his/her own questionnaire on the patient's clinical status, progression of the disease, and preferred treatment for the patient. The physician's data are stored in an input module. The physician also indicates his/her opinions on all treatment options for the condition, given the system's data sets on the outcomes of each. These data sets are updated via literature reviews and consultations with clinicians to interpret their significance. Attachment 1 is a printout setting forth an on-line question for patients and physicians for mitral valve disease. The answers are processed by the CHES system and result in a report. See Attachment 2 which is sample CHES report for an imaginary patient Sally E. Spencer with mitral valve disease.

The users (patient, physician, and insurer) receive outcome data (morbidity and mortality rates) on each treatment. They are told that these statistics are compiled from many published studies and must only be used to compare outcomes in their own geographic area. This resembles Prudential Insurance's program of paying patients' travel expenses to centers with the best outcomes on specific procedures.

The data entered by the patient and physician users is immediately integrated and quantified by the system. Certain data is used by the system to estimate direct and indirect costs for each treatment option. These costs appear both on the physician/patient report generated by the system and on the report sent to insurers. The reports can be sent within minutes electronically, or by mail to all parties after the completion of both questionnaires.

All parties (physicians, patients, and insurers) will thus have more information than is now available to assess the costs, risks, and benefits of each treatment option for one condition. Patients and physicians can more knowledgeably discuss the merits of each option both from clinical and non-clinical perspectives, permitting more informed treatment choices. Insurers, without intruding on the physician-patient relationship, will know the nature and extent of the patient's condition, the treatment preferred, and how it compares to other options in terms of outcomes and costs (direct and indirect). This minimizes the need of insurers to inquire about the appropriateness of care. Insurers, who now pay for second opinions and programs to control health care costs, should cover this information service. These costs continue to rise, illustrating the ineffectiveness of such measures. The informative value of second opinions depends on differences in training, experience, and the practice patterns of immediate peers of the second physician. The opinion rendered may or may not differ from the treatment preferred by the first physician. While CHES consults medical experts as well, its outcome projections reflect statistically verified pattern differences in outcomes among treatments using many well-documented, published studies on treatment results to maximize the accuracy of the information provided. Treatment, disease subcategories, concurrent conditions (related or unrelated), patient demographics, and any effect of recent medical advances in each treatment stratify the data from these studies as they may affect outcomes of one treatment over another. These elements are then used to evaluate the costs, risks, and benefits of competing treatments.

Figure 1:
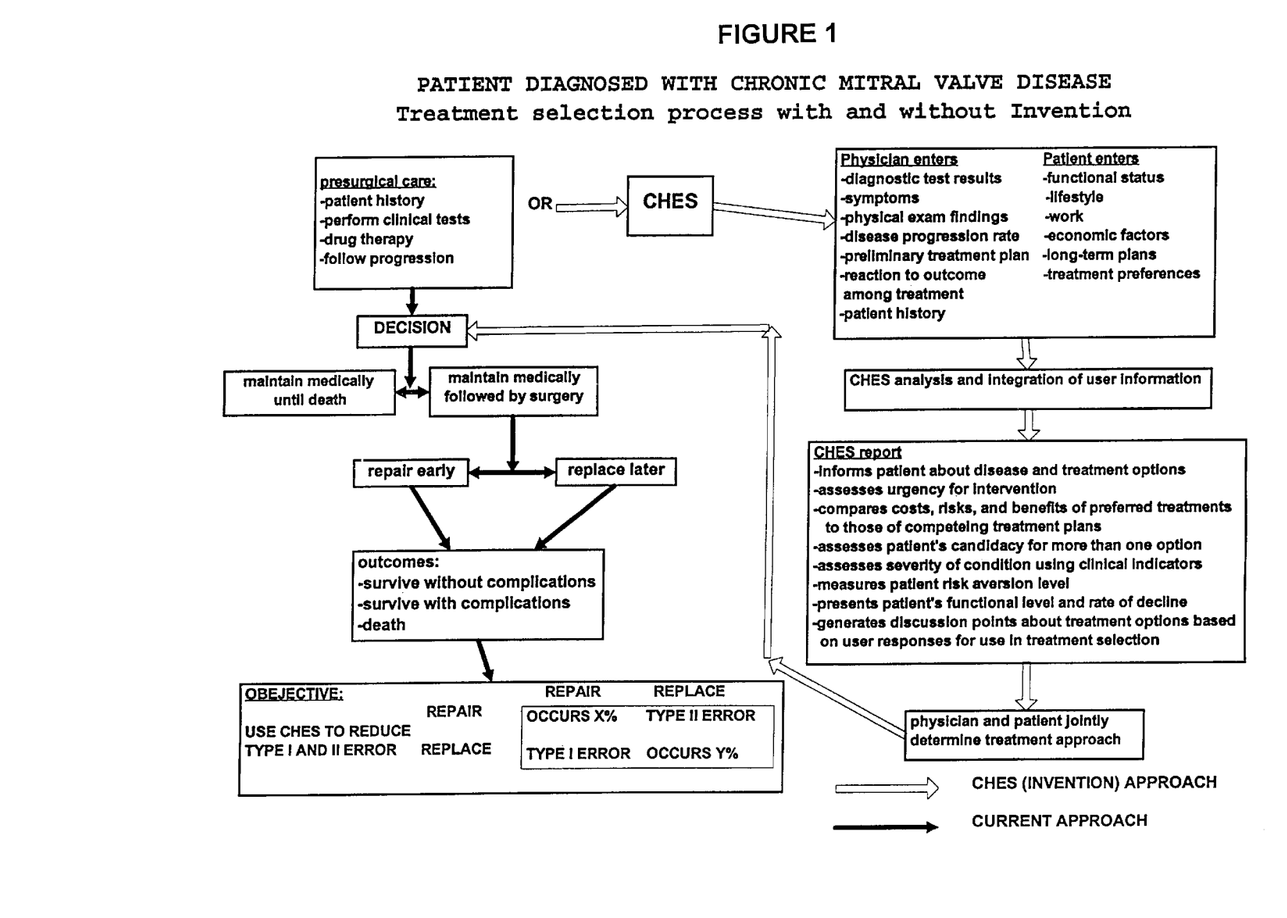
FIG. 1 is a flowchart comparing the approach of the invention compared to that of prior art methods.

Chart 1 sets forth how a CHES system for chronic mitral valve disease would work compared to present treatment selection option.

Figure 2:
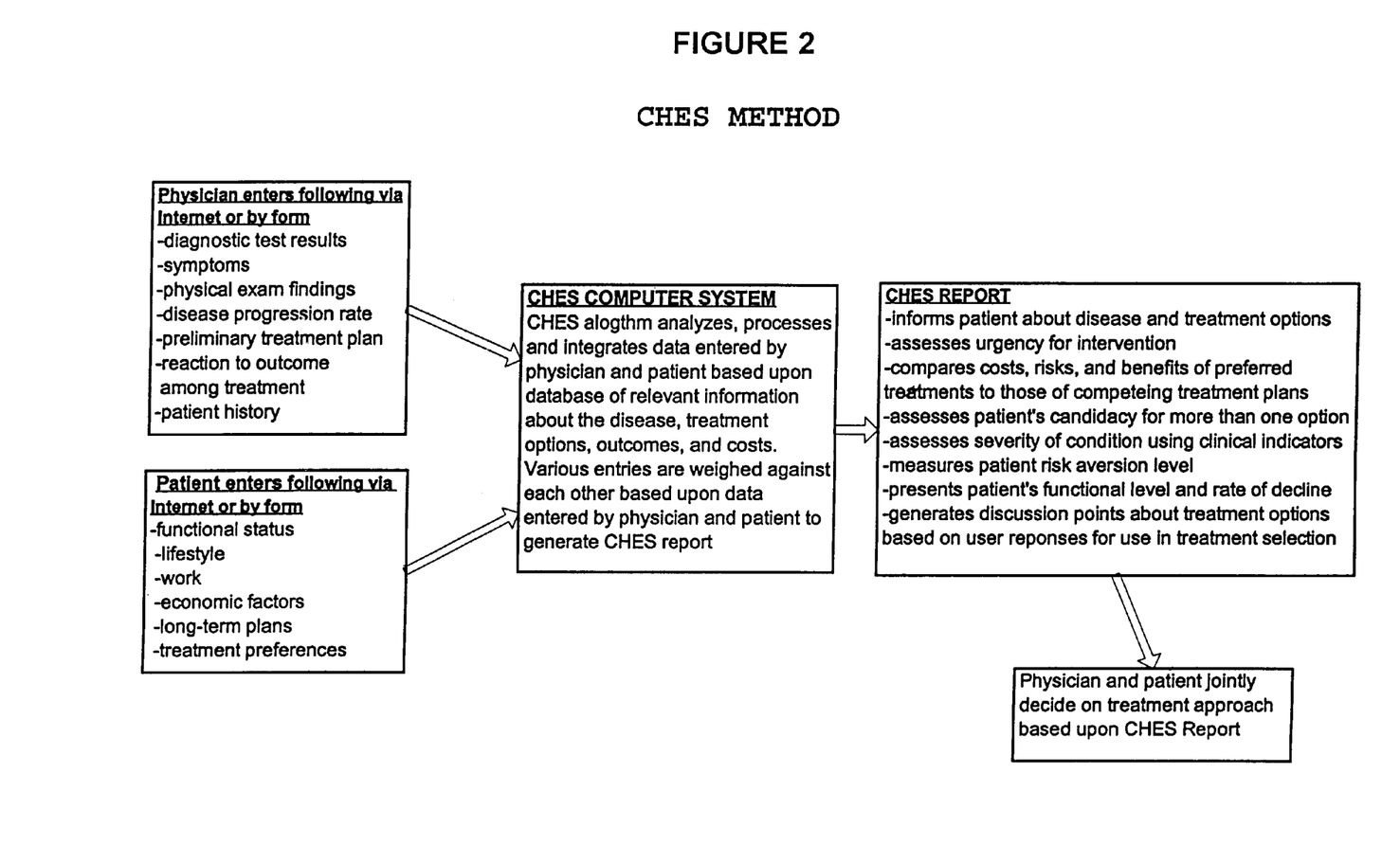
FIG. 2 is a flowchart illustrating the CHES system and method of the invention.

Chart 2 describes the CHES method in more detail.

Building a CHES System:

CHES derives much value in its unique development process outlined below.

1. Describing the Disease:
    a. Determine the etiologies, forms, and natural history of a disease.
    b. Determine its incidence and prevalence rates in the population.
    c. Identify all treatments that can be used.
    d. Identify how patient factors, lesion, and severity of disease dictate treatment.
    e. Resolve whether one treatment is favored despite factors in each case, and why.
2. Assessing Treatments:
    a. Collect and analyze treatment outcome data from published follow-up studies.
    b. Stratify data by specific lesion of disease, treatment used, demographics, and time frame.
    c. Document (for further investigation) whether treatments are selected based on clinical factors or as a matter of practice style.
    d. Ascertain any correlation between treatments and patient factors, or practice style, (e.g., treat early symptoms vs. not treating until symptoms are serious).
    e. Use the treatment with the statistically best outcomes as the basis for a risk assessment scale for computing patients' risk tolerance level.
    f. Prepare interview schedule on disease, customary and lesser-used treatments for known medical experts (who may differ in their views) to explain in terms of practice patterns. Have them score specific clinical indicators for treatment, and give three value ranges for each indicator; Normal, Suspect, and Severe.
    g. Ask experts to reconcile practice views with published outcomes statistics to assess effect of practice patterns on treatment selection.
    h. Conduct cost-effectiveness analysis to compare costs of each treatment to survival, continued morbidity, and mortality.
3. System Components
    a. Use cost and outcome data, from the steps above, to indicate trade-offs for patients to consider in selecting, with their physicians, a suitable treatment.
    b. Quantify these trade-offs using discount rates to score patients' risk tolerance for each treatment strategy, showing the proximity of treatment preferences to what is most cost-effective.
    c. Develop patient questionnaire to elicit treatment preferences and their bases, e.g., economic, family, lifestyle, and fear of surgical risk, pain, etc., which may change his/her risk tolerance level.
    d. Develop physician questionnaire on patients' clinical condition, severity level, planned treatment, and why others are not appropriate for a given patient.
    e. Apply risk tolerance scale to the reasons for preferences to construct a risk tolerance profile of the patient.

f. Use cost-effectiveness analysis results to compute estimated direct medical cost of treatment and indirect costs resulting from inability to work or perform other tasks measurable by the concept of human capital.

g. Write conditional text for each possible physician and patient questionnaire response, explaining its positive or negative impact on outcome.

h. Format a report showing the responses and conditional text, the patient's risk tolerance profile, patient and physician treatment preferences, how they compare to that found to be most cost-effective, and the factors supporting their choice. Compute direct and indirect costs of each treatment option. Also, show the patient's severity level based on aggregate scores of the clinical indicators. Provide a one-page summary of the same information for use by insurers.

At this point, each system will be shown to physicians at different centers for comments and suggested changes, followed by testing with other physicians and their pre-treatment patients. Care will be taken to ensure properly selected patients and to prevent use of this test to make an actual treatment decision. They are only to use the system and provide feedback as to its utility and its accuracy in profiling the clinical and non-clinical factors in each case.

Figure 3:
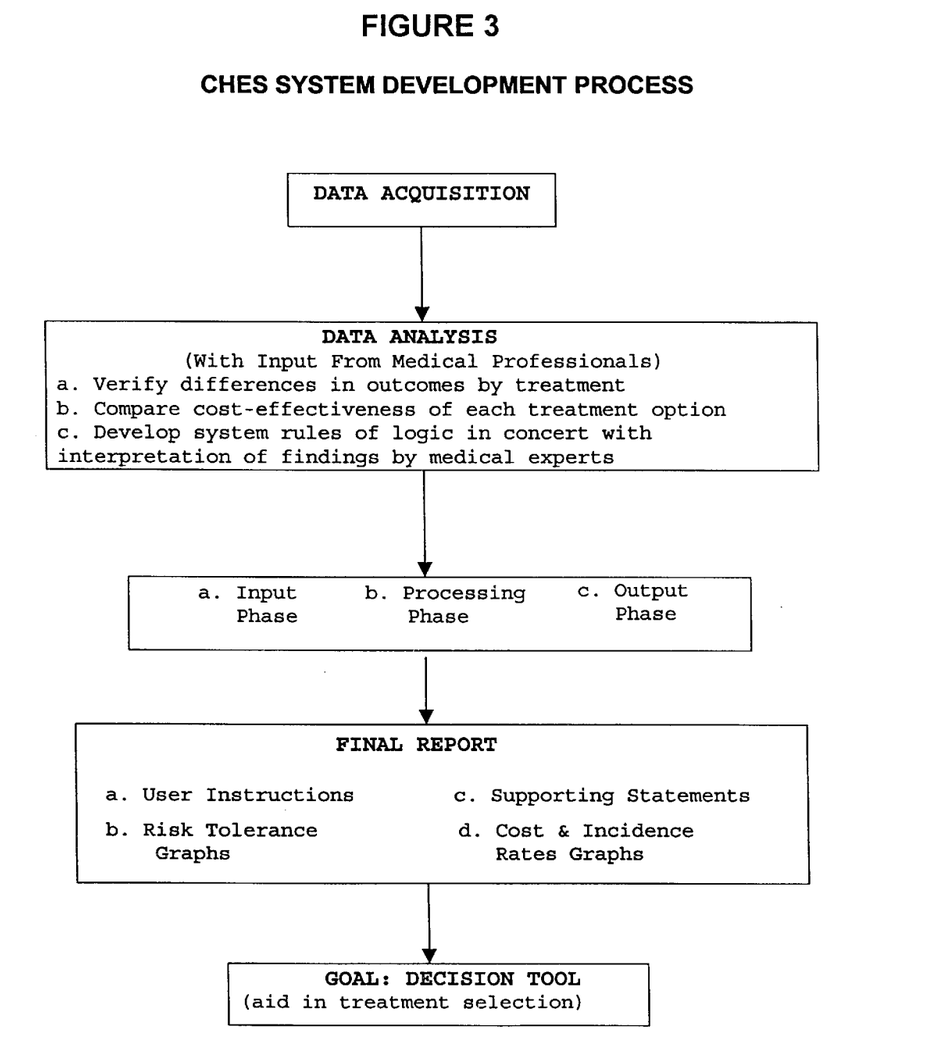
FIG. 3 is a flowchart illustrating the CHES system development process.

Chart 3 sets forth the CHES system development process in general. This development process will be repeated for all systems, with variations as needed to accommodate different diseases and their treatments. This process is tedious and will require varying amounts of time to complete for each system. It is for this reason that this plan projects a three-year development time frame. Ways will be sought to expedite this process without compromising accuracy.

The intricacy of this process requires a staff highly trained in health economics, health services delivery, statistics, software engineering, and medicine. The start-up and operating budgets for this venture reflect this need. Further, CHES will have ongoing system updates to assure that they reflect the latest in medical knowledge and treatment technology. These continual updates will prevent the systems from becoming obsolete.

This process of combining economic principles with clinical data distinguishes CHES from all other computer aids in medicine. The system's areas of inquiry and other components include:

a. Socioeconomic, Functional and Clinical Status
b. Patient's Level of Responsibility (e.g. family, work, social, etc.)
c. Related Symptoms and Episodes of Illness
d. Current Treatment Plan
e. Patient and Physician Treatment Preferences
f. Physician's Views on Surgical Intervention
g. Post-operative Morbidity and Mortality Rates
h. Assignment of Risk Aversion Values
i. Overall Cost, (i.e., Direct and Indirect Cost based on Patient's own Discount Rate)

Risk values are based on data entered by patients and physicians, and are shown numerically and in bar graphs. Answers are scored on the patient risk tolerance scale ranging from 0 to 9. Physicians indicate the patients' clinical status by entering values for clinical indicators (e.g. hemodynamic data, EKG results, echocardiography data, etc., for MVD). These values are compared to preset threshold values, to assess whether a patient needs surgery.

The cost of each treatment is computed based on the type of MVD, patient income and discount rate, major post-operative complication rates, and the direct costs of surgery. In later versions, costs will also be specific to treatment sites. A copy of a sample report for a patient with mitral valve disease is attached as Appendix 2.

The report is labeled as an aid in deciding the need for, timing, and type of treatment. While it highlights the most cost-effective option based on medical literature and expert medical opinions, it informs physicians and patients of the costs, risks, and benefits of all treatments, and records the reasons for their choice. This is because generally less optimal treatments can be more cost-effective depending on the unique factors of each case. This approach will be used in the other systems.

In addition to CHES systems for mitral valve disease, a series of CHES systems directed to many other diseases and conditions, including but not limited to the following, would be very helpful:

| | PROCEDURE | ANNUAL NO. |
|---|---|---|
| 1. | Mitral Valve Surgery | 40,000 |
| 2. | Arthroplasty & Hip Replacement | 130,000 |
| 3. | Hysterectomy: | |
| | Abdominal | 475,000 |
| | Vaginal | 164,000 |
| | TOTAL | 639,000 |
| 4. | Cholecystectomy | 449,000 |
| 5. | Coronary Artery Bypass Graft | 230,000 |
| 6. | Operations of the Ear | 429,000 |
| 7. | Breast Cancer Surgery | |
| | Tissue Excision | 109,000 |
| | Mastectomy | 116,000 |
| | TOTAL | 225,000 |
| TOTAL ANNUAL PROCEDURES | | 2,142,000 |

These figures represent the number of these treatments within recent 12-month periods. They do not reflect the prevalence of the underlying conditions, which comprises several times the number of annual procedures. It is these larger patient populations and their potential costs to insurers that such a service will impact. For example, there are approximately 200,000 pre-surgical MVD patients who would be candidates for the use of the service yearly.

Over time, CHES will develop additional systems for less severe conditions and procedures (e.g. tonsillectomy, eye surgery, etc.). However, the most immediate application will likely be on major conditions with high costs and significant differences in risks and outcomes based on the treatment selected.

Data Acquisition and Analysis:

The steps in designing the CHES systems are noted above. Treatment outcome data is collected from the medical literature, and statistically tested to determine the validity of observed outcome patterns. This approach (Meta-Analysis) is highly regarded by researchers. It involves analyzing results from other studies, to form new conclusions on the efficacies of different treatments. It is acceptance by scientific authorities that the Meta-Analysis approach enhances the credibility of CHES in collecting and analyzing published outcome data. The results of this process are then combined with charge data to compute the direct and indirect costs of each treatment. They are then presented to outside medical panels to review in terms of current practice patterns. Their comments, along with the outcome and cost data sets, form the basis for the rules to be used in developing each system.

The CHES System:
1. Input Phase (either on-line using a terminal or through a manual):
   a. Patient Section
   Give information on condition, treatment options, and glossary of key terms. Elicit data on functional status, family roles, commitments, impact of illness on life-styles and activities, future plans, and expectations from treatment.
   b. Physician Section
   Elicit information about patient's clinical and functional status, anticipated course of treatment, patient's candidacy for surgery, etc. Obtain opinions on each treatment option.
   c. Provide up-to-date clinical outcome data on each option for consideration.
2. Processing Phase:
   a. Cost formulas for a set time frame for each treatment option. (Components of formulas: direct and indirect medical costs, complication rates, mortality rates, potential loss of earnings, discount rates.)
   b. Discount rates assigned to responses to quantify each patient's risk tolerance.
   c. Preassigned levels of risk (0–9 scale) for each possible response are computed.
   d. Different data sets of post-treatment complication incidence rates are selected depending on the type of lesion.
   e. Text representing physician's and patient's responses are generated.
3. Output Phase:
   a. Data entered is quantified and integrated into a hard-copy report on real time basis.
   b. Graphics and conditional text are included to enhance user interpretation.

Report Components:
1. Instructions for using the report as an aid in the overall treatment selection process.
2. A graph of the patient's risk profile based on clinical and non-clinical factors.
3. Text based on physician and patient responses to which both parties can refer, especially in assessing any high-risk item in the patient's risk tolerance profile.
4. A graph comparing the post-operative complication probabilities for each treatment option.
5. Estimated short and long-term costs for each treatment option.

Benefits of CHES

The benefits of CHES to physicians, patients, institutions, third party payers, and UR firms include the following:
1. Physicians
   More patient data with which to better select treatments.
   Access to the latest data on costs, risks, and benefits associated with each treatment option.
   Higher possibility of cost-containment in their practice.
   Critique of current treatment plan for review and study.
   Reduced exposure to professional liability.
2. Patients
   Access to data on their diagnosis, and treatment options.
   Objective appraisal of their medical condition in the context of their overall health, economic, family, and social activity.
   Outcome data with which to judge potential consequences and expectations of treatment options.
   More information with which to discuss treatment options with family members as part of decision-making process.
3. Institutions
   Better UR based on extensive documentation of preferred treatment.
   More patients due to a wider range of procedures per condition.
   More data with which to estimate and control use of resources, and conduct long range planning (e.g., expanding cardiac units, greater patient mix and volume).
   Greater chance of certification as Preferred Provider Organizations via the cost containment benefits of CHES.
   Improved competitive posture relative to competitors by improving cost-containment capabilities of the system.
   Reduced exposure to legal liability.
4. Utilization Review Organizations
   Advanced assessment of propriety and cost of preferred treatments.
   Ability to alert employer clients of questionable treatment plans so that appropriate inquiries can be made, before such plans are approved or disapproved.
   Higher probability of reducing health care costs.
5. Third Party Payers
   Assurance that physician and patient have considered all treatment options before making final choice.
   Ability to compare preferences to competing options in terms of associated potential long-term expenditures on a case by case basis.
   Extensive documentation on merits of preferred treatment.
   Information with which to consult with the physician when the preferred treatment does not appear optimal, either from a clinical or cost perspective.
   Ability to assess choice of high cost treatments and where appropriate, encouraged use of lower cost treatments with comparable or better probable outcomes.
   More flexibility to competitively adjust premium rates due to cost savings.

While all of these entities will benefit from CHES, insurers will gain the most by reducing their financial risk. Government, university, and private studies show that many treatments are either misprescribed or overused, while their alternatives would have been more effective. The morbidity and mortality caused by ineffective treatments add to the cost of health care.

Insurers use various means to control health care costs for their employer clients. However, basing health care on its dollar cost alone is ineffective and may raise costs. For example, a provider who charges less for a procedure has an incentive to prescribe it more often. "Volume discounts" in the short-term can result in higher long-term costs, if the increased use of discounted procedures causes more morbidity and/or mortality among those patients for whom other procedures would have been more effective. Since clinicians agree that the efficacies of many treatments they prescribe are unknown, the long-term effectiveness of treatments which patients receive must be verified. CHES can provide this assurance, thus minimizing avoidable health care costs. Disability and term life insurance companies will also benefit from CHES by lowering the probability of paying for long-term disability and/or premature death. Since health insurers will benefit directly, CHES will focus marketing strategies toward them. They, in turn, will be able to require physicians and patients to use the CHES systems, just as they currently require second opinion, pre-certification, and utilization review procedures.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in a generic and descriptive sense only and not for the purpose of limitation, the scope of the invention being delineated in the following the claims which follow.

I claim:

1. A computerized health evaluation system for joint patient and physician treatment decision making concerning particular medical diseases and conditions, comprising a computer system having:

a database of the latest medical findings concerning the particular disease and condition and their treatment options and the outcomes, costs, risks, and benefits associated therewith;

a patient input module for patient input of patient factors concerning the patient's lifestyle and treatment preferences;

a physician input module for physician input of physical and physiological information; and an algorithm for weighting the patient's information and the physician's findings in view of the database and for generating a graphical report which graphically displays the potential risks and benefits of all viable treatment options based upon the weighting of the patient data and the physician input of physical and physiological factors in view of the database so that the patient and physician can make a more informed medical decision.

2. The computerized health evaluation system of claim 1, wherein the patient and physician enter patient information and physical and physiological information in electronic form via a computer network.

3. The computerized health evaluation system of claim 1, wherein the patient and physician enter patient factors and physical and physiological findings respectively via at least one of an interactive telephone system, questionnaire forms submitted via facsimile, and via questionnaire forms manually entered or scanned into the computer system.

4. The computerized health evaluation system of claim 1, wherein the patient information comprises functional status, patient lifestyle, work factors, economic factors, long term plans, and treatment preferences.

5. The computerized health evaluation system of claim 1, wherein the physical and physiological information comprises diagnostic test results, symptoms, physical exam findings, disease progression rate, preliminary treatment plan, reactions to outcomes across treatments, and patient history.

6. The computerized health evaluation system of claim 1, wherein the report generated includes information that informs the patient about the particular disease and condition and treatment options, assesses urgency for intervention, compares costs, risks and benefits of any identified preferred treatment to those of competing treatment plans, assesses the patient's candidacy for more than one option, assesses the severity of the disease and condition using clinical indicators, quantifies patient risk aversion level, presents patient's functional level and rate of decline, and discussion points about treatment options based on patient and physician inputs to facilitate in treatment selection.

7. The computerized health evaluation system of claim 1, wherein the patient and physician will jointly decide on a treatment approach based upon the report.

8. A method for computerized health evaluation for joint patient and physician decision making concerning particular medical diseases and conditions, comprising the following steps:

providing a computer system having a patient input module for patient input of patient information concerning the patient's lifestyle and preferences, a physician input module for physician input of physical and physiological findings, a database of the latest medical findings concerning the particular disease and condition, and a computer algorithm for weighting the patient factors and the physician findings in view of the database and generating a graphical report setting forth various treatment options based upon the weighting of the patient factors and the physician input of physical and physiological findings in view of the database so that the patient and physician can make a more informed medical decision;

having the patient enter the patient's functional status, lifestyle, work factors, economic factors, long term plans, and treatment preferences in the patient input module;

having the physician enter physical and physiological findings comprising diagnostic test results, symptoms, physical exam findings, disease progression rate, preliminary treatment plan, reaction to outcome among treatment, and patient history into the physician input module;

using the computer algorithm for processing and weighting the patient factors and physical and physiological findings in view of the database to determine the potential risks and benefits of each viable treatment options based upon the patient factors and the physical and physiological findings in view of the database;

generating a graphical report that includes information that informs the patient about the particular disease and condition and treatment options, assesses urgency for intervention, compares costs, risks and benefits of any identified preferred treatment to those of competing treatment plans, assesses the patient's candidacy for more than one option, assesses the severity of the disease and condition using clinical indicators, quantifies patient risk aversion level, presents patient's functional level and rate of decline, and discussion points about treatment options based on patient and physician inputs for use in treatment selection; and having the patient and physician jointly decide on the treatment based upon the graphical report.

* * * * *